(12) United States Patent
Makarenko et al.

(10) Patent No.: US 11,154,211 B2
(45) Date of Patent: Oct. 26, 2021

(54) TISSUE DAMAGE ASSESSMENT METHOD AND SYSTEM

(71) Applicant: NOKOMIS, INC., Charleroi, PA (US)

(72) Inventors: Vladimir Makarenko, McDonald, PA (US); James Robert Uplinger, II, Cranberry Township, PA (US)

(73) Assignee: NOKOMIS, INC., Charleroi, PA (US)

( * ) Notice: Subject to any disclaimer, the term of this patent is extended or adjusted under 35 U.S.C. 154(b) by 210 days.

(21) Appl. No.: 16/245,283

(22) Filed: Jan. 11, 2019

(65) Prior Publication Data

US 2020/0221971 A1 Jul. 16, 2020

(51) Int. Cl.
*A61B 5/0538* (2021.01)
*G06K 9/62* (2006.01)
*A61B 5/0537* (2021.01)

(52) U.S. Cl.
CPC .......... *A61B 5/0538* (2013.01); *G06K 9/6218* (2013.01); *A61B 5/0537* (2013.01)

(58) Field of Classification Search
None
See application file for complete search history.

(56) References Cited

U.S. PATENT DOCUMENTS

| | | | | |
|---|---|---|---|---|
| 6,078,047 | A * | 6/2000 | Mittleman | G01N 21/49 250/330 |
| 8,473,215 | B2 * | 6/2013 | Walther | G06F 16/55 702/19 |
| 9,295,402 | B1 * | 3/2016 | Arbab | G01N 21/3586 |
| 9,686,173 | B1 * | 6/2017 | Giordano | H04L 43/0864 |
| 10,448,864 | B1 * | 10/2019 | Uplinger, II | A61B 5/082 |
| 2010/0268223 | A1 * | 10/2010 | Coe | G06T 7/11 606/41 |
| 2017/0257297 | A1 * | 9/2017 | Mathew | H04L 41/0893 |
| 2018/0028079 | A1 * | 2/2018 | Gurevich | G06K 9/6274 |
| 2020/0221971 | A1 * | 7/2020 | Makarenko | A61B 5/0538 |

* cited by examiner

*Primary Examiner* — Tahmina N Ansari
(74) *Attorney, Agent, or Firm* — AP Patents; Alexander Pokot

(57) ABSTRACT

A method and system to assess data from a dielectric probe to determine the health of tissue by denoising the data and clustering the data points. The assessment is used to assist medical professionals in the care patients.

19 Claims, 6 Drawing Sheets

TISSUE DAMAGE ASSESSMENT METHOD AND SYSTEM

BACKGROUND OF INVENTION

The assessment of damaged tissue by burn or other cause has been done visually. Surgical intervention and debridement are often the treatment of choice. The visual presentation of tissue obscures the extent and condition of tissue. The underlying condition of damaged tissue whether dead, impaired or healthy is not readily determined visually.

BRIEF SUMMARY OF INVENTION

The technical problem is to take noisy dielectric data from probes to assess tissue damage. The solution is cluster data preferably using a dimensionless machine learning algorithm. There is no practical way to map such data to show tissue damage in near real time without machine learning.

The preferred embodiment is to take a density clustering algorithm, such as Density based Spatial Clustering of Application with Noise (DBSCAN), and to train it with data from burn patients. The algorithm clusters the data and determines the boundary of data point clusters. By training the algorithm and adjusting criteria such as distance measure, distance between data points, the minimum data points constituting a cluster and data density. Clusters of healthy tissue and damaged tissue emerges. Data density is also measured by the maximum distance between data points. The algorithm is validated with further validation data. The clusters are then mapped onto two and three dimensions. A map of clustered data can be displayed to guide surgeons and other healthcare professionals in the treatment of damaged tissue.

DETAILED DESCRIPTION OF INVENTION

Figure 1A:
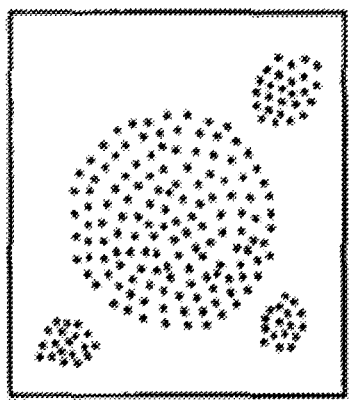
FIG. 1A is an illustration of well defined and separated data clusters.

The state of healthy, damaged and dead tissue can be determined from the dielectric response from far field probes. The technical problem is to take noisy permittivity data and identify the state of the tissue mapping it in 2 and 3 dimensions. The technical solution is to use machine learning algorithms to cluster the data points that are relevant to tissue assessment and to ignore the noise datapoints. There are multiple clustering algorithms. The preferred algorithm is a DBSCAN because it does not require knowledge of the number of clusters and is dimensionless. The algorithm Density Based Spatial Clustering of Applications with Noise (DBSCAN) is designed to discover the clusters and noise in a database according to definitions. DBSCAN calculates values by defining the neighborhood of a Point P. A naïve approach could require for each point in a cluster that there are at least a minimum number of points (MinPts) the neighborhood of that point. Ideally, the parameters of epsilon (nearness) and MinPts would be known for each cluster and at least one point from the respective cluster. Using these parameters, one could retrieve all points that are density-reachable from the given point using the correct parameters. There is no simple way to know this for all clusters of the data set. However, there is a simple and effective heuristic to determine epsilon and MinPts of the least dense cluster in the data set by using a global value for each parameter for all clusters. The density parameters of the least dense cluster are used for these global parameter values specifying the lowest density which is not considered to be noise.

Pseudo Code for an implementation of a clustering algorithm is as follows:

```
DBSCAN (SetOfPoints, Eps, MinPts)
// SetOfPoints is UNCLASSIFIED
ClusterId := nextId(NOISE);
FOR i FROM 1 TO SetOfPoints.size DO
Point := SetOfPoints.get(i);
IF Point.CiId = UNCLASSIFIED THEN
IF ExpandCluster(SetOfPoints, Point,
ClusterId, Eps, MinPts) THEN
ClusterId := nextId(ClusterId)
END IF
END IF
END FOR
END; // DBSCAN
```

Where the SetOfPoints is the set of points of the received dielectric response data, Eps is epsilon, measure of nearness, and MinPts is the minimum number of points in a cluster.

The most important function used by DBSCAN is ExpandCluster which is presented below:

```
ExpandCluster (SetOfPoints, Point, CiId, Eps, MinPts) : Boolean;
seeds : =SetOfPoints. regionQuery (Point, Eps )
IF seeds.size<MinPts THEN // no core point
SetOfPoint. changeCl Id (Point, NOISE)
RETURN False;
ELSE // all points in seeds are density-
// reachable from Point
SetOfPoints. changeCiIds ( seeds, C1 Id)
seeds .delete (Point)
WHILE seeds <> Empty DO
currentP := seeds.first( )
result := setofPoints.regionQuery(currentP, Eps)
IF result.size >= MinPts THEN
FOR i FROM 1 TO result.size DO
resultP := result.get(i)
IF resultP. CiId
IN (UNCLASSIFIED, NOISE}THEN
IF resultP.CiId = UNCLASSIFIED THEN
seeds, append (resultP)
END IF;
SetOfPoints. changeCiId ( resultP, CiId)
END IF; // UNCLASSIFIED or NOISE
END FOR;
END IF; // result.size >= MinPts
seeds, delete (currentP)
END WHILE; // seeds <> Empty
RETURN True;
END IF
END; // ExpandCluster
```

Figure 1B:
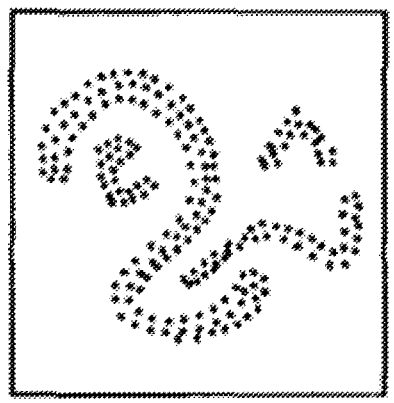
FIG. 1B is an illustration of non-linearly separated data clusters.
Figure 1C:
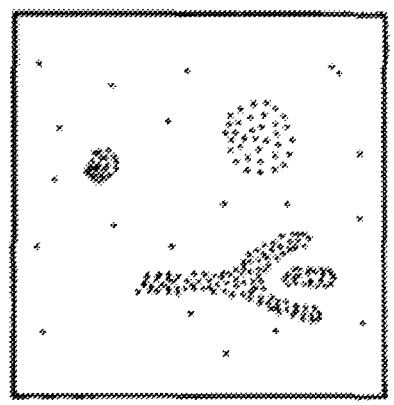
FIG. 1C illustration of clustering of noisy data.

When looking at the sample sets of points depicted in FIG. 1A-1C, unambiguously illustrates clusters of points and noise points not belonging to any of those clusters. As result, it is possible then to separate the noise.

Figure 2:
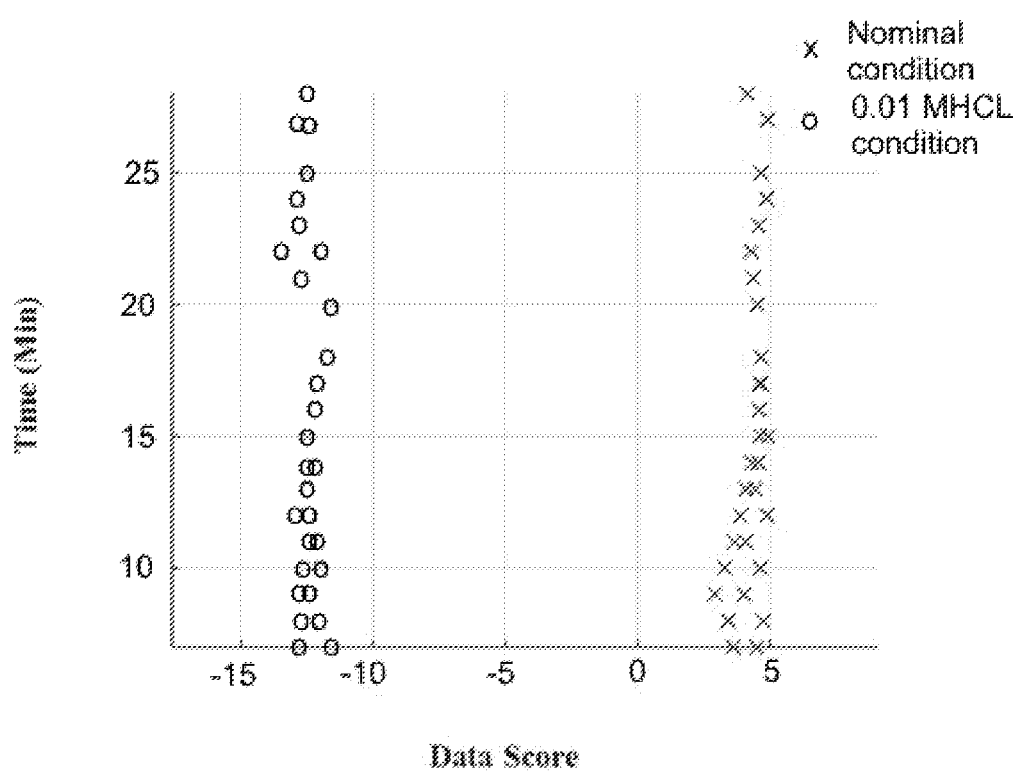
FIG. 2 is an illustration of the dielectric response of nominal and stressed tissue of a data score against a time scale.
Figure 3:
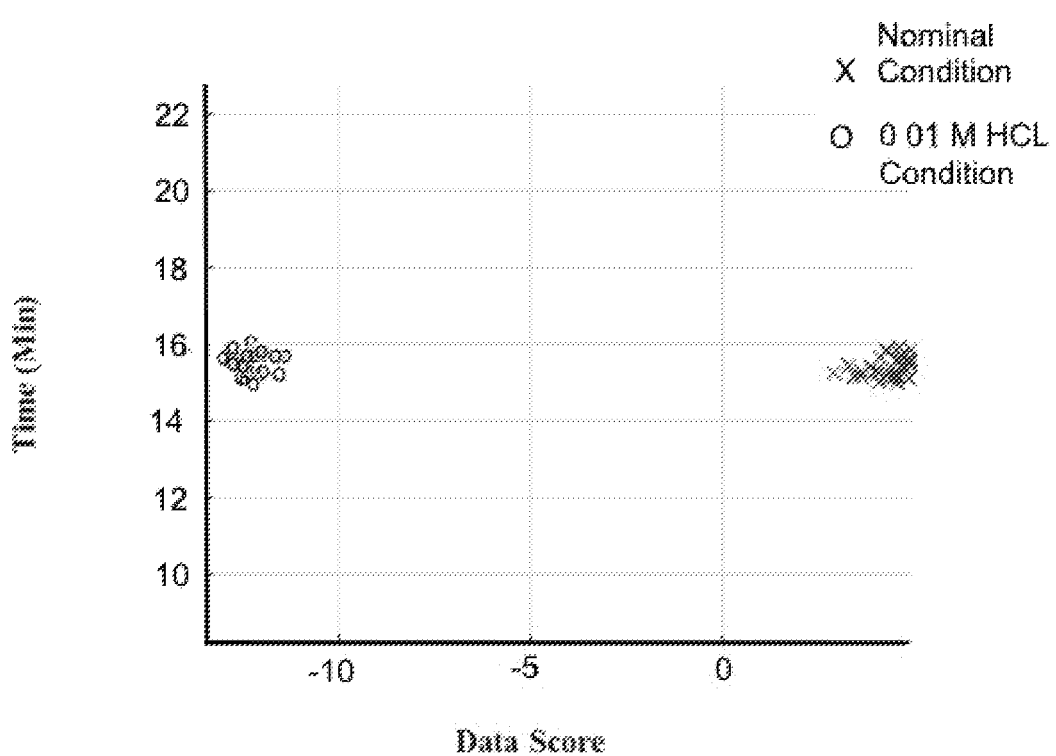
FIG. 3 is an illustration of the dielectric response of nominal tissue and stressed tissue of data score using a normalized time scale.
Figure 4:
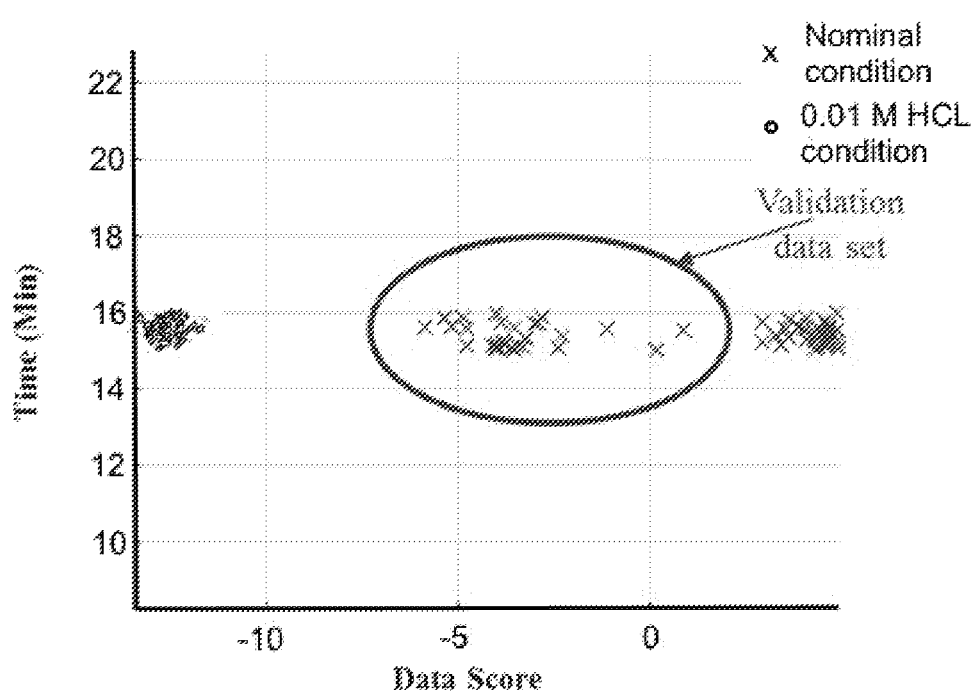
FIG. 4 is an illustration of the clustering dielectric response with nominal and stressed validation data clusters.

FIGS. 1A and 1B are illustrations of the data clustering of experimental data in which cultured cells dielectric response is shown for untreated cultures and cultures that are stressed by a 0.01 MHCL solution. The FIG. 1C shows the data with noise. Similarly, FIG. 2 shows a set of data points for a nominal and 0.01 MHCL stressed culture. The dielectric response is separable and consistent over time. Similarly, in FIG. 3 the nominal and 0.01 MHCL data points cluster separately. The separation in a controlled laboratory environment is a basis for denoising a dielectric response of cells that are nominal and stressed. FIG. 4 shows results for clustering of validation data.

The differing dielectric response identifies differing tissue states (types). In this case the cell health of nominal and stressed cells.

The System

Figure 5:
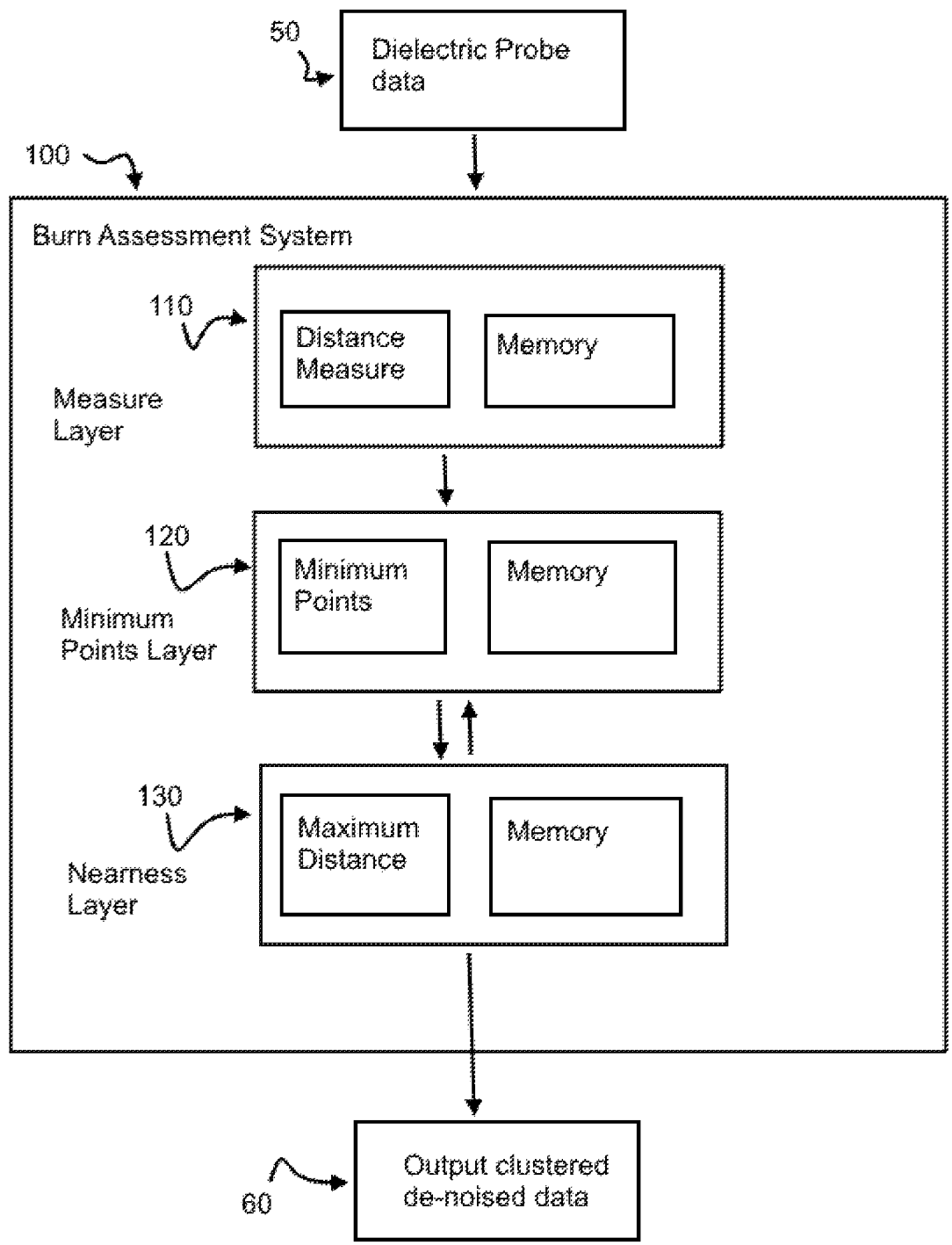
FIG. 5 is a block diagram of an embodiment of the system.

The system 100, FIG. 5, receives data from a dielectric probe 50. The probe measures the permittivity of tissue. The cell health of the tissue affects the permittivity. Healthy (nominal) cells have a different permittivity than cells that are stressed, damaged or dead. However, the data is noisy and it is difficult to separate the cell conditions. The system 100 is labeled burn assessment system, but it can be used to distinguish any cells that have different permittivity. The system 100 has three (3) layers, a measure layer 110, a minimum points layer 120, and a nearness layer 130. Each layer has a processing portion and a memory portion. The layer portions are referred to as units.

The distance measure is the manner that distance between data points are measured. Different measures are more appropriate for different tissue geometries. Preferably, the measure is cartesian along a Euclidean line or polar along a curve.

However, other measures such as hyperbolic curves would be more appropriate for certain geometries.

The distance measure portion applies the measure to the data and the measure and resulting data point distance are retained in memory and passed on to a minimum points layer 120.

The minimum points layer 120 has a minimum points measure that defines the minimum number of points that define a cluster. The minimum points measure is applied to the distance measured data points. The minimum points measure, and data points are retained in memory. This is passed to a maximum distance (nearness) layer 130 for define the boundary points of the resulting clusters.

The system begins with a selected measure, minimum points measure, and maximum distance (nearness) measure. The system varies the minimum points and nearness parameters preferably where the clustering separation is stable. However, the varying of parameters for a selected number of variances, varying only one of the minimum point or nearness parameters or a combination of these would also be within the denoising system.

The system is embodied vary the minimum points parameter and nearness parameters. The minimum points parameter can be held constant while varying the nearness parameter. The nearness parameter can be held constant while varying the minimum points parameter. Both parameters can be varied as well.

Once the clustering is completed, the data points not in the clusters are noise and are removed and outputted 60. The data can be mapped onto n-dimensions preferably two or three dimensions.

The Method

Figure 6:
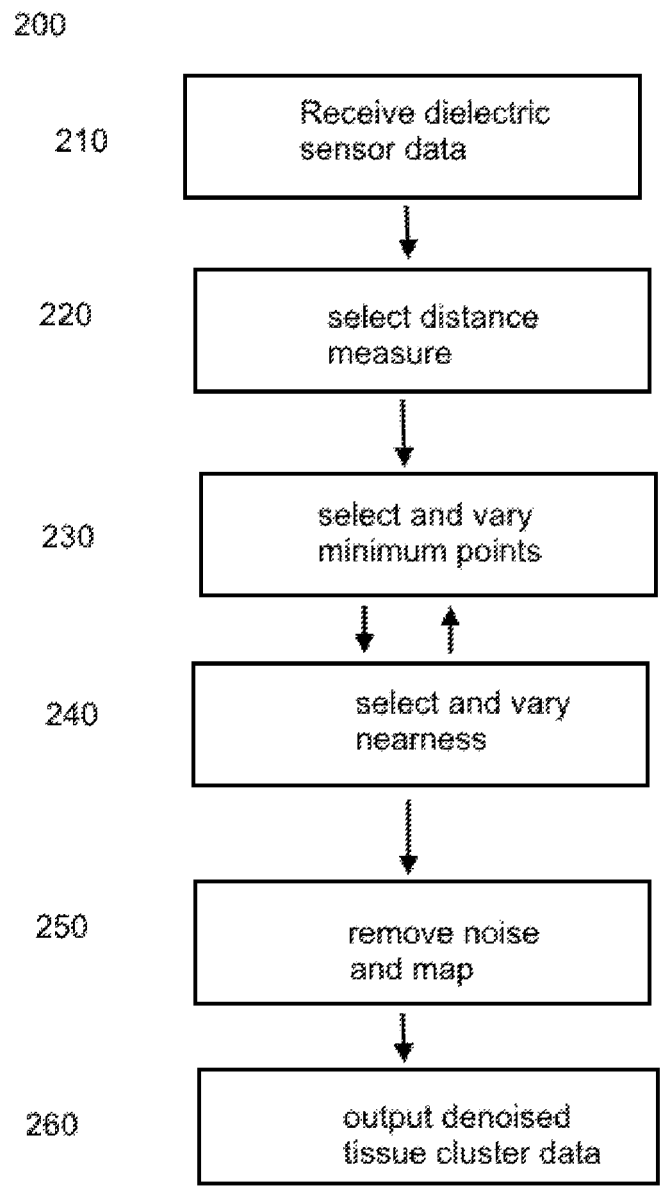
FIG. 6 is a flow chart of the method.

Data is processed by clustering the data according to similar data points. FIG. 6 is a flow chart of the method 200. The method 200, FIG. 6, takes data from a dielectric probe or sensor 210. A distance measure as previously described is selected and the distance between data points is measured. A minimum number of points that define a cluster is selected 230 and a nearness measure that defines the cluster density is selected 240. The minimum points and nearness parameter are preferably successively varied. However, one of the parameters can be held constant and only one varied or a combination of these selections and variance.

The method is embodied vary the minimum points parameter and nearness parameters. The minimum points parameter can be held constant while varying the nearness parameter. The nearness parameter can be held constant while varying the minimum points parameter. Both parameters can be varied as well. The parameters are varied preferably until the separation between clusters is stable. However, the number of variations of parameters until the separation is maximized or after a selected number of variations.

The data points that are not within a cluster are defined as noise and are removed 250 and the result is out put as denoised cluster data. The data can be mapped onto n-dimensions preferably two or three dimensions.

The de-noised data can be used to guide medical treatment of tissue that is not visibly damaged, or the damage is concealed. The damaged or in some way different tissue can be assessed and removed. The clustered data points that are denoised can be displayed for surgeons and medical professional or could be used for robotic surgery.

Although specific advantages have been enumerated above, various embodiments may include some, none, or all of the enumerated advantages. Other technical advantages may become readily apparent to one of ordinary skill in the art after review of the following figures and description.

It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

Unless otherwise specifically noted, articles depicted in the drawings are not necessarily drawn to scale.

Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

We claim:

1. A method of de-noising a dielectric probe data from a tissue, said method comprising:

in a response to received dielectric probe data containing measurements of the tissue permittivity, identifying a tissue type by a dielectric response;

clustering by varying, with a trained and validated dimensionless clustering algorithm, one or both of a minimum number of data points within a cluster and a maximum distance between said data points within said cluster to determine a boundary of said cluster; and discarding, as noise, data points that are not on said boundary or within an interior of said cluster;

de-noised data points, when mapped, assessing tissue damage.

2. The method of claim 1 wherein said dimensionless clustering algorithm comprises a DBSCAN.

3. The method of claim 1 wherein there is an additional step of mapping data points that are on said boundary and within said interior of said cluster onto n-dimensional space.

4. The method of claim 1 wherein there is an additional step of mapping said data points onto at least one of 2 and 3 dimensional spaces.

5. A method of de-noising dielectric probe data from a tissue, said method comprising:

in a response to a received dielectric probe data, clustering said dielectric probe data by a trained and validated dimensionless clustering algorithm to create one or more clusters;

identifying cluster boundary data points of a cluster;

discarding data points not within said cluster or on a boundary of said cluster;

mapping remaining data points that are on said boundary and within said cluster onto n-dimensional space; and outputting said mapping to assess tissue damage.

6. The method of claim 5 where said clustering by said dimensionless clustering algorithm comprises a DBSCAN.

7. The method of claim 5 wherein said clustering by said dimensionless clustering algorithm comprises:

selecting a minimum number of data points within said cluster;

selecting a maximum distance between said data points within said cluster;

varying said maximum distance between said data points within said cluster; and comparing resulting clusters to maximize compactness and contiguity.

8. The method of claim 5 wherein said clustering by said dimensionless clustering algorithm has further steps of:

selecting a maximum distance between said data points;

selecting a minimum number of data points within said cluster;

varying said minimum number of said data points within said cluster; and comparing resulting clusters for compactness and contiguity.

9. The method of claim 5 wherein said clustering by said dimensionless clustering algorithm comprises:

selecting a maximum distance between data points within said cluster;

selecting a minimum number of said data points within said cluster;

varying said minimum number of said data points within said cluster;

varying said maximum distance between said data points within said cluster; and comparing, for each combination of said minimum distance between said data points and minimum number of said data points within said cluster, resulting clusters for compactness and contiguity.

10. The method of claim 5 wherein said clustering by said dimensionless clustering algorithm comprises:

selecting a maximum distance between data points within said cluster;

selecting a minimum number of said data points within said cluster;

selecting a number of instances to vary said maximum distance between said data points within said cluster;

selecting a number of instances to vary said maximum distance between datapoints within a cluster;

varying said minimum number of data points within said cluster;

varying, for each of said varied minimum number of said data points within said cluster, said maximum distance between said data points within said cluster; and comparing, for each combination of said minimum distance between said data points and a minimum number of said data points within said cluster, resulting clusters for compactness and contiguity.

11. A method of de-noising a dielectric probe to assess tissue damage data having a training data set, a validation data set and a testing data set of permittivity data from said dielectric probe, said method comprising:

in a response to a received testing data set, processing said testing data set with a clustering algorithm trained with said training data set and validated with said validation data set;

mapping resulting clusters onto a n-dimensional space;

selecting for said trained and validated clustering algorithm a parameter of data point distance;

selecting for said trained and validated clustering algorithm a parameter or data point nearness;

selecting for said trained and validated clustering algorithm a value of minimum points for a cluster;

varying successively each of said data point nearness parameter and said value of minimum points until an algorithm clustering variation is generally stable;

discarding non-clustered data points that are classified as noise; and mapping clusters, after discarding said non-clustered data points, onto said n-dimensional space;

mapped clusters assessing the tissue damage.

12. The method of claim 11 wherein said n-dimensional space comprises one of a 2-dimensional space and a 3-dimensional space.

13. The method of claim 11 wherein selecting clustering algorithm measure of data point distance that is one of rectilinear and polar.

14. The method of claim 11 wherein training of said validated clustering algorithm comprises:

selecting a parameter of data point nearness;

selecting a parameter of minimum points for said cluster;

varying successively each of said parameters resulting in clustering;

comparing resulting clusters;

discarding non-clustered data points that are classified as noise; and mapping clusters onto said n-dimensional space.

15. A dielectric probe de-noising system, comprising:

a distance layer that has a distance measure processing portion unit and a memory portion unit, said distance measure processing portion measuring data points received from said dielectric probe, said memory portion retaining resulting data point distance;

a minimum point layer having a cluster minimum datapoint processing portion and a memory portion; and a nearness layer having a nearness processing portion unit and a memory portion unit;

said minimum point layer and nearness layer successively varying a minimum point parameter and a nearness parameter to produce clustering;

said nearness layer defining boundaries of resulting clusters;

data points, received from said dielectric probe, that are not within said resulting clusters, being removed to result in de-noised data points;

said de-noised data points assessing tissue damage.

16. The dielectric probe de-nosing system of claim 15 wherein the distance measure layer applies a distance measure that is one of rectilinear and polar.

17. The dielectric probe de-nosing system of claim 15 wherein said successive varying of said minimum point parameter and said nearness parameter is a selected number of combinations of minimum points and nearness.

18. The method of claim 11, wherein non-clustered data points comprise data points that are outside of cluster boundaries.

19. The dielectric probe de-noising system of claim 15, wherein said dielectric probe comprises a far field dielectric probe.

* * * * *